United States Patent
Casey et al.

(10) Patent No.: US 11,439,514 B2
(45) Date of Patent: Sep. 13, 2022

(54) SYSTEMS AND METHODS FOR ORTHOPEDIC IMPLANT FIXATION

(71) Applicant: CARLSMED, INC., Carlsbad, CA (US)

(72) Inventors: Niall Patrick Casey, Carlsbad, CA (US); Michael J. Cordonnier, Carlsbad, CA (US)

(73) Assignee: Carlsmed, Inc., Carlsbad, CA (US)

( * ) Notice: Subject to any disclaimer, the term of this patent is extended or adjusted under 35 U.S.C. 154(b) by 91 days.

(21) Appl. No.: 16/383,215

(22) Filed: Apr. 12, 2019

(65) Prior Publication Data
US 2019/0321193 A1    Oct. 24, 2019

Related U.S. Application Data

(60) Provisional application No. 62/658,389, filed on Apr. 16, 2018.

(51) Int. Cl.
*A61F 2/44* (2006.01)
*A61B 17/70* (2006.01)
(Continued)

(52) U.S. Cl.
CPC ........ *A61F 2/4455* (2013.01); *A61B 17/7058* (2013.01); *A61B 17/8033* (2013.01);
(Continued)

(58) Field of Classification Search
CPC ........ A61B 2017/568; A61B 2034/108; A61B 17/7059; A61B 2034/102; A61B 2034/105; A61B 2034/101; A61B 2034/104
See application file for complete search history.

(56) References Cited

U.S. PATENT DOCUMENTS

| 4,704,686 A | 11/1987 | Aldinger |
| 4,936,862 A | 6/1990 | Walker et al. |

(Continued)

FOREIGN PATENT DOCUMENTS

| CN | 104318009 A | 1/2015 |
| CN | 104353121 A | 2/2015 |

(Continued)

OTHER PUBLICATIONS

Endo, Kenji et al. "Measurement of whole spine sagittal alignment using the SLOT radiography of the SonialVision safire series clinical application." Medical Now, No. 78; Aug. 2015, 4 pages.
(Continued)

*Primary Examiner* — David W Bates
(74) *Attorney, Agent, or Firm* — Perkins Coie LLP

(57) ABSTRACT

A personalized fixation system includes a surgical planning software tool configured to adjust relationships of relevant anatomy of a subject, at least one bone anchor, a plate having a shape that does not conform to a single plane, the plate configured to accept the at least one bone anchor, wherein the shape of the plate is at least partially determined by the surgical planning software tool, and wherein the plate includes at least one node having a hole configured to receive the at least one bone anchor, and a locking element configured to connect the at least one bone anchor to the plate, wherein the plate is manufactured using additive manufacturing.

21 Claims, 14 Drawing Sheets

(51) Int. Cl.
   *A61B 34/10* (2016.01)
   *A61F 2/30* (2006.01)
   *A61B 17/80* (2006.01)

(52) U.S. Cl.
   CPC .......... *A61B 34/10* (2016.02); *A61F 2/30749* (2013.01); *A61B 2034/102* (2016.02); *A61F 2/30965* (2013.01); *A61F 2/442* (2013.01)

(56) References Cited

U.S. PATENT DOCUMENTS

| | | |
|---|---|---|
| 5,431,562 A | 7/1995 | Andreiko et al. |
| 6,696,073 B2 | 2/2004 | Boyce et al. |
| 6,772,026 B2 | 8/2004 | Bradbury |
| 6,932,842 B1 | 8/2005 | Litschko et al. |
| 6,978,188 B1 * | 12/2005 | Christensen ....... A61B 17/8863 700/118 |
| 6,988,241 B1 | 1/2006 | Guttman |
| 7,174,282 B2 | 2/2007 | Hollister et al. |
| 7,187,790 B2 | 3/2007 | Sabol et al. |
| D548,242 S | 8/2007 | Viegers |
| 7,747,305 B2 | 6/2010 | Dean et al. |
| 7,756,314 B2 | 7/2010 | Karau et al. |
| 7,799,077 B2 | 9/2010 | Lang |
| 8,246,680 B2 | 8/2012 | Betz |
| 8,265,949 B2 | 9/2012 | Haddad |
| 8,275,594 B2 | 9/2012 | Lin |
| 8,337,507 B2 | 12/2012 | Lang |
| 8,394,142 B2 | 3/2013 | Bertagnoli |
| 8,457,930 B2 | 6/2013 | Shroeder |
| 8,532,806 B1 | 9/2013 | Masson |
| 8,556,983 B2 | 10/2013 | Bojarski et al. |
| 8,644,568 B1 | 2/2014 | Hoffman |
| 8,735,773 B2 | 5/2014 | Lang |
| 8,758,357 B2 | 6/2014 | Frey |
| 8,775,133 B2 | 7/2014 | Schroeder |
| 8,781,557 B2 | 7/2014 | Dean |
| 8,843,229 B2 | 9/2014 | Vanasse |
| 8,855,389 B1 | 10/2014 | Hoffman |
| 8,870,889 B2 | 10/2014 | Frey |
| 9,020,788 B2 | 4/2015 | Lang |
| 9,198,678 B2 | 12/2015 | Frey et al. |
| 9,208,558 B2 | 12/2015 | Dean |
| D761,842 S | 7/2016 | Johnson |
| 9,411,939 B2 * | 8/2016 | Furrer ................ A61B 17/8071 |
| 9,445,907 B2 | 9/2016 | Meridew |
| 9,452,050 B2 | 9/2016 | Miles et al. |
| 9,542,525 B2 | 1/2017 | Arisoy et al. |
| 9,642,633 B2 | 5/2017 | Frey et al. |
| 9,693,831 B2 | 7/2017 | Mosnier et al. |
| 9,707,058 B2 | 7/2017 | Bassett |
| 9,715,563 B1 | 7/2017 | Schroeder |
| 9,757,245 B2 | 9/2017 | O'Neil et al. |
| 9,775,680 B2 | 10/2017 | Bojarski et al. |
| 9,782,228 B2 | 10/2017 | Mosnier et al. |
| 9,993,341 B2 | 6/2018 | Vanasse |
| 10,034,676 B2 | 7/2018 | Donner |
| 10,089,413 B2 | 10/2018 | Wirx-Speetjens et al. |
| D841,675 S | 2/2019 | Hoffman |
| 10,213,311 B2 | 2/2019 | Mafhouz |
| D845,973 S | 4/2019 | Jaycobs |
| D845,974 S | 4/2019 | Cooperman |
| D847,165 S | 4/2019 | Kolbenheyer |
| D848,468 S | 5/2019 | Ng |
| D849,029 S | 5/2019 | Cooperman |
| D849,773 S | 5/2019 | Jiang |
| 10,292,770 B2 | 5/2019 | Ryan |
| 10,299,863 B2 | 5/2019 | Grbic et al. |
| 10,390,958 B2 | 8/2019 | Maclennan |
| D860,237 S | 9/2019 | Li |
| D860,238 S | 9/2019 | Bhardwaj |
| D867,379 S | 11/2019 | Ang |
| D867,389 S | 11/2019 | Jamison |
| 10,463,433 B2 | 11/2019 | Turner et al. |
| D870,762 S | 12/2019 | Mendoza |
| 10,512,546 B2 | 12/2019 | Kamer et al. |
| 10,517,681 B2 | 12/2019 | Roh et al. |
| D872,117 S | 1/2020 | Kobayashi |
| D872,756 S | 1/2020 | Howell |
| D874,490 S | 2/2020 | Dodsworth |
| D875,761 S | 2/2020 | Heffernan |
| D876,454 S | 2/2020 | Knowles |
| D877,167 S | 3/2020 | Knowles |
| D879,112 S | 3/2020 | Hejazi |
| 10,588,589 B2 | 3/2020 | Bregman-Amitai et al. |
| 10,603,055 B2 | 3/2020 | Donner et al. |
| D880,513 S | 4/2020 | Wang |
| D881,908 S | 4/2020 | Sunil |
| D881,910 S | 4/2020 | Lin |
| 10,621,289 B2 | 4/2020 | Schroeder |
| 10,631,988 B2 | 4/2020 | Arnold et al. |
| 10,646,236 B2 | 5/2020 | Donner et al. |
| 10,646,258 B2 | 5/2020 | Donner et al. |
| 10,736,698 B2 | 8/2020 | Bohl |
| 10,751,188 B2 | 8/2020 | Guo et al. |
| 10,806,597 B2 | 10/2020 | Sournac et al. |
| 10,902,944 B1 | 1/2021 | Casey et al. |
| 11,000,334 B1 | 5/2021 | Young |
| 2002/0007294 A1 | 1/2002 | Bradbury et al. |
| 2004/0171924 A1 | 9/2004 | Mire et al. |
| 2005/0049590 A1 | 3/2005 | Alleyne et al. |
| 2005/0271996 A1 | 12/2005 | Sporbert et al. |
| 2006/0009780 A1 | 1/2006 | Foley |
| 2007/0118243 A1 * | 5/2007 | Schroeder .............. G16H 50/50 700/118 |
| 2007/0276501 A1 * | 11/2007 | Betz .................... A61F 2/30942 623/17.16 |
| 2008/0161680 A1 | 7/2008 | von Jako |
| 2008/0195240 A1 * | 8/2008 | Martin ............... A61B 17/8061 700/98 |
| 2010/0191088 A1 | 7/2010 | Anderson |
| 2010/0292963 A1 * | 11/2010 | Schroeder ............. G16H 50/50 703/1 |
| 2011/0218545 A1 | 9/2011 | Catanzarite et al. |
| 2011/0301710 A1 | 12/2011 | Mather et al. |
| 2012/0010710 A1 * | 1/2012 | Frigg .................... A61B 34/20 623/16.11 |
| 2012/0084064 A1 | 4/2012 | Dzenis et al. |
| 2012/0116203 A1 * | 5/2012 | Vancraen ............... A61B 34/10 600/407 |
| 2012/0150243 A9 * | 6/2012 | Crawford .............. G16H 50/50 606/86 R |
| 2012/0191192 A1 | 7/2012 | Park |
| 2012/0287238 A1 | 11/2012 | Onishi |
| 2012/0296433 A1 | 11/2012 | Farin |
| 2013/0211531 A1 | 8/2013 | Steines et al. |
| 2014/0072608 A1 | 3/2014 | Karagkiozaki |
| 2014/0074438 A1 * | 3/2014 | Furrer ................... G16H 50/50 703/1 |
| 2014/0081659 A1 | 3/2014 | Nawana et al. |
| 2014/0086780 A1 | 3/2014 | Miller |
| 2014/0164022 A1 | 6/2014 | Reed |
| 2014/0263674 A1 | 9/2014 | Cerveny |
| 2014/0350614 A1 | 11/2014 | Frey |
| 2015/0105891 A1 | 4/2015 | Golway et al. |
| 2015/0324490 A1 | 11/2015 | Page |
| 2015/0328004 A1 | 11/2015 | Mafhouz |
| 2016/0015465 A1 | 1/2016 | Steines et al. |
| 2016/0074048 A1 | 3/2016 | Pavlovskaia |
| 2016/0117817 A1 | 4/2016 | Seel |
| 2016/0143744 A1 | 5/2016 | Bojarski et al. |
| 2016/0210374 A1 | 7/2016 | Mosnier et al. |
| 2016/0217268 A1 | 7/2016 | Otto |
| 2016/0242857 A1 | 8/2016 | Scholl |
| 2016/0300026 A1 | 10/2016 | Bogoni et al. |
| 2016/0354039 A1 | 12/2016 | Soto et al. |
| 2016/0378919 A1 | 12/2016 | McNutt et al. |
| 2017/0000566 A1 | 1/2017 | Gordon |
| 2017/0014169 A1 | 1/2017 | Dean |
| 2017/0020679 A1 | 1/2017 | Maclennan |
| 2017/0035514 A1 | 2/2017 | Fox et al. |
| 2017/0061375 A1 | 3/2017 | Laster |
| 2017/0068792 A1 | 3/2017 | Reiner |

(56) References Cited

U.S. PATENT DOCUMENTS

| | | |
|---|---|---|
| 2017/0135706 A1 | 5/2017 | Frey et al. |
| 2017/0143494 A1 | 5/2017 | Mahfouz |
| 2017/0143831 A1 | 5/2017 | Varanasi et al. |
| 2017/0216047 A1 | 8/2017 | Hawkes et al. |
| 2017/0220740 A1 | 8/2017 | D'Urso |
| 2017/0252107 A1 | 9/2017 | Turner et al. |
| 2017/0262595 A1 | 9/2017 | Vorhis |
| 2017/0354510 A1 | 12/2017 | O'Neil et al. |
| 2017/0367645 A1 | 12/2017 | Klinder |
| 2018/0008349 A1* | 1/2018 | Gillman ............. A61F 2/4455 |
| 2018/0116727 A1* | 5/2018 | Caldwell ............ G16H 50/50 |
| 2018/0168499 A1 | 6/2018 | Bergold |
| 2018/0168731 A1 | 6/2018 | Reid |
| 2018/0185075 A1* | 7/2018 | She ................ A61B 17/8071 |
| 2018/0233222 A1 | 8/2018 | Daley |
| 2018/0233225 A1 | 8/2018 | Experton |
| 2018/0250075 A1 | 9/2018 | Cho |
| 2018/0303552 A1 | 10/2018 | Ryan |
| 2018/0303616 A1 | 10/2018 | Bhattacharyya et al. |
| 2018/0338841 A1 | 11/2018 | Miller et al. |
| 2019/0029757 A1 | 1/2019 | Roh et al. |
| 2019/0146458 A1 | 5/2019 | Roh et al. |
| 2019/0167435 A1 | 6/2019 | Cordonnier |
| 2019/0201106 A1 | 7/2019 | Siemionow |
| 2019/0262084 A1 | 8/2019 | Roh et al. |
| 2019/0282367 A1 | 9/2019 | Casey et al. |
| 2019/0328929 A1 | 10/2019 | Kugler et al. |
| 2019/0380782 A1* | 12/2019 | McAfee ............... G16H 30/40 |
| 2019/0380792 A1 | 12/2019 | Poltaretskyi et al. |
| 2020/0078180 A1 | 3/2020 | Casey et al. |
| 2020/0085509 A1 | 3/2020 | Roh et al. |
| 2020/0138519 A1* | 5/2020 | Frey .................... A61B 34/10 |
| 2020/0170802 A1 | 6/2020 | Casey et al. |
| 2020/0289288 A1 | 9/2020 | Müller et al. |
| 2020/0311318 A1* | 10/2020 | Suddaby ............. A61B 90/06 |
| 2020/0315708 A1 | 10/2020 | Mosnier et al. |
| 2020/0345420 A1* | 11/2020 | Hobeika ............ A61B 17/7002 |
| 2021/0059822 A1 | 3/2021 | Casey et al. |
| 2021/0210189 A1 | 7/2021 | Casey et al. |
| 2021/0244447 A1* | 8/2021 | Schroeder .............. A61B 34/10 |
| 2021/0382457 A1 | 12/2021 | Roh et al. |
| 2022/0000556 A1 | 1/2022 | Casey et al. |
| 2022/0000625 A1 | 1/2022 | Cordonnier |
| 2022/0039965 A1 | 2/2022 | Casey et al. |
| 2022/0047402 A1 | 2/2022 | Casey et al. |

FOREIGN PATENT DOCUMENTS

| | | |
|---|---|---|
| CN | 204468348 U | 7/2015 |
| CN | 105796214 A | 7/2016 |
| CN | 108670506 A | 10/2018 |
| CN | 110575289 A | 12/2019 |
| CN | 111281613 A | 6/2020 |
| CN | 112155792 A | 1/2021 |
| EP | 3120796 A1 | 1/2017 |
| WO | 2004110309 A2 | 12/2004 |
| WO | 2010151564 A1 | 12/2010 |
| WO | 2014180972 A2 | 11/2014 |
| WO | 2016172694 A1 | 10/2016 |
| WO | 2019112917 A1 | 6/2019 |
| WO | 2019148154 A1 | 8/2019 |

OTHER PUBLICATIONS

International Searching Authority, International Search Report and Written Opinion, PCT Patent Application PCT/US2018/063530, dated Feb. 12, 2019, 16 pages.

Materialise Mimics, "Efficiently turn scans into accurate virtual 3D models," <www.materialize.com/en/medical/software/mimics>, 1 page.

Pimenta, Dr. Luiz, "Current Surgical Strategies to Restore Proper Sagittal Alignment," Journal of Spine 2015, vol. 4, Issue 4, 2 pages.

International Search Report and Written Opinion for International Application No. PCT/US19/50885, dated Jan. 28, 2020 (21 pages).

International Search Report and Written Opinion for International Application No. PCT/US19/63855, dated Feb. 14, 2020 (15 pages).

U.S. Appl. No. 15/985,409 for Ryan, filed Apr. 21, 2017.

Extended European Search Report for European Application No. 18885367.5, dated Aug. 16, 2021, 8 pages.

International Search Report and Written Opinion for International Application No. PCT/US21/44878, dated Nov. 16, 2021, 18 pages.

International Search Report and Written Opinion for International Application No. PCT/US21/45503, dated Jan. 11, 2022, 19 pages.

International Search Report and Written Opinion for International Patent Application No. PCT/US21/12065, dated Apr. 29, 2021, 19 pages.

International Search Report and Written Opinion for International Patent Application No. PCT/US21/59837, dated Feb. 7, 2022, 19 pages.

Majdouline et al., "Preoperative assessment and evaluation of instrumentation strategies for the treatment of adolescent idiopathic scoliosis: computer simulation and optimization." Scoliosis 7, 21 (2012), pp. 1-8.

* cited by examiner

SYSTEMS AND METHODS FOR ORTHOPEDIC IMPLANT FIXATION

INCORPORATION BY REFERENCE TO ANY PRIORITY APPLICATIONS

This application claims the benefit of priority to U.S. Provisional Patent Application No. 62/658,389, filed on Apr. 16, 2018, which is herein incorporated by reference in its entirety for all purposes. Priority is claimed pursuant to 35 U.S.C. § 119.

FIELD OF THE INVENTION

The field of the invention generally relates to orthopedic implants, including spinal implants, and methods for designing and producing them.

BACKGROUND

Orthopedic implants are used to correct a variety of different maladies. Orthopedic surgery utilizing orthopedic implants may include one of several specialties, including: hand surgery, shoulder and elbow surgery, total joint reconstruction (arthroplasty), skull reconstruction, maxillofacial reconstruction, pediatric orthopedics, foot and ankle surgery, spine surgery, musculoskeletal oncology, surgical sports medicine, and orthopedic trauma. Spine surgery may encompass one or more of the cervical, thoracic, lumbar spine, sacrum, pelvis, or ilium, and may treat a deformity or degeneration of the spine, or related back pain, leg pain, or other body pain. Irregular spinal curvature may include scoliosis, lordosis, or kyphosis (hyper- or hypo-). Irregular spinal displacement may include spondylolisthesis. Other spinal disorders include osteoarthritis, lumbar degenerative disc disease or cervical degenerative disc disease, lumbar spinal stenosis or cervical spinal stenosis.

Spinal fusion surgery may be performed to set and hold purposeful changes imparted on the spine. Spinal surgeries typically include hardware or implants to help fix the relationship between anatomical structures such as vertebral bodies and nerves. In many instances, fixation devices or implants are affixed to bony anatomy to provide support during healing. These implants are often made of polymers or metals (including titanium, titanium alloy, stainless steel, cobalt chrome, or other alloys). These fixation implants can be described as anchors, screws, nuts, bolts, rivets, rods, connectors, tethers, or other fasteners. Each implant may be designed to mate with the anatomy or other implants in order to provide a construct to allow relief of symptoms and encourage biologic healing.

Spinal surgeons are often relied upon to treat patients with spinal deformities, such as scoliosis. These surgical treatments may require re-alignment of spinal anatomy and preservation of the re-alignment in order to relieve symptoms. Surgeons manipulate the spine using instruments and implants that mate with bony anatomy. Adjustment of the instruments and implants connected to the bony anatomy can produce the desired alignment of the spinal anatomy. When the alignment of the spinal anatomy is achieved intra-operatively, the preservation of that alignment is required in order to provide post-operative relief of symptoms. Fixation implants can be used to provide a construct to maintain the correction achieved by the surgeon while bony fusion occurs.

Additionally, spinal fusion procedures include PLIF (posterior lumbar interbody fusion), ALIF (anterior lumbar interbody fusion), TLIF (transverse or transforaminal lumbar interbody fusion), or LLIF (lateral lumbar interbody fusion), including DLIF (direct lateral lumbar interbody fusion) or XLIF (extreme lateral lumbar interbody fusion). One goal of interbody fusion is to grow bone between vertebrae in order to seize (e.g., lock) the spacial relationships in a position that provides enough room for neural elements, including exiting nerve roots. An interbody implant (interbody device, interbody implant, interbody cage, fusion cage, or spine cage) is a prosthesis used between vertebral bodies in spinal fusion procedures to maintain relative position of the vertebrae and establish appropriate foraminal height and decompression of exiting nerves.

Each patient may have individual or unique disease characteristics, but most device solutions include implants (e.g. rods, screws, interbody implants) having standard sizes or shapes.

SUMMARY OF THE INVENTION

In one embodiment of the present disclosure, a personalized fixation system includes a surgical planning software tool configured to adjust relationships of relevant anatomy of a subject, at least one bone anchor, a plate having a shape that does not conform to a single plane, the plate configured to accept the at least one bone anchor, wherein the shape of the plate is at least partially determined by the surgical planning software tool, and wherein the plate includes at least one node having a hole configured to receive the at least one bone anchor, and a locking element configured to connect the at least one bone anchor to the plate, wherein the plate is manufactured using additive manufacturing.

In another embodiment of the present disclosure, a personalized fixation system includes a surgical planning software tool configured to adjust relationships of relevant anatomy of a subject, at least one bone anchor, a plate having a shape that does not conform to a single plane, the plate configured to accept the at least one bone anchor, wherein the shape of the plate is at least partially determined by the surgical planning software tool, and wherein the plate includes at least one node having a hole configured to receive the at least one bone anchor, and a locking element configured to connect the at least one bone anchor to the plate, wherein the plate is manufactured using subtractive manufacturing.

In yet another embodiment of the present disclosure, a method for manufacturing a fixation system includes capturing anatomy using digital imaging software, segmenting relevant anatomy of a subject from irrelevant anatomy using the imaging software, correcting the anatomy in virtual space using surgical planning software, designing implants using software, and building implants using additive manufacturing.

In still another embodiment of the present disclosure, a system for designing an implant system includes a computational system configured to perform anatomical adjustments, an algorithm for determining position of bony structures, an algorithm for determining configuration of the implant system, an algorithm for determining sizes, densities, construction, and shape of an implant, an algorithm for determining shape and location of nodes, holes, longitudinal elements, locking elements, and construction of a posterior plate, an algorithm for determining length, width, diameter, density, and construction of bone anchors, an algorithm for determining the start-point and trajectory for delivery of bone anchors, and an additive manufacturing technique configured to build implants of the implant system.

In yet another embodiment of the present disclosure, a system for designing an implant system includes a computational system to perform virtual surgery of a subject, an algorithm for determining position of bony structures of the subject, an algorithm for determining shape, composition, and position of implants, and an additive manufacturing technique to build the implants.

In still another embodiment of the present disclosure, a system for designing a fixation system includes a computational system to perform virtual surgery of a subject, an algorithm for determining optimal position of bony structures in the subject, an algorithm for determining optimal shape of the fixation system including location of nodes, bone anchors, longitudinal elements, and locking elements, an algorithm for determining optimal bone anchor length, width, start-point, and trajectory, an algorithm for determining optimal number, position, shape, density, and internal structure of implants of the fixation system, and an additive manufacturing technique to build the implants.

In yet another embodiment of the present disclosure, a method for manufacturing a personalized fixation system includes providing a surgical planning software tool configured to adjust relationships of relevant anatomy of a subject, capturing anatomy and anatomic relationships using digital imaging software, segmenting relevant anatomy from irrelevant anatomy, correcting the relevant anatomy in virtual space, designing one or more of node locations, node shapes, hole locations, hole angles, hole sizes, hole shapes, longitudinal element shape, longitudinal element thickness, and longitudinal element density of a fixation plate, and manufacturing the fixation plate using additive manufacturing techniques.

DETAILED DESCRIPTION

Figure 1:
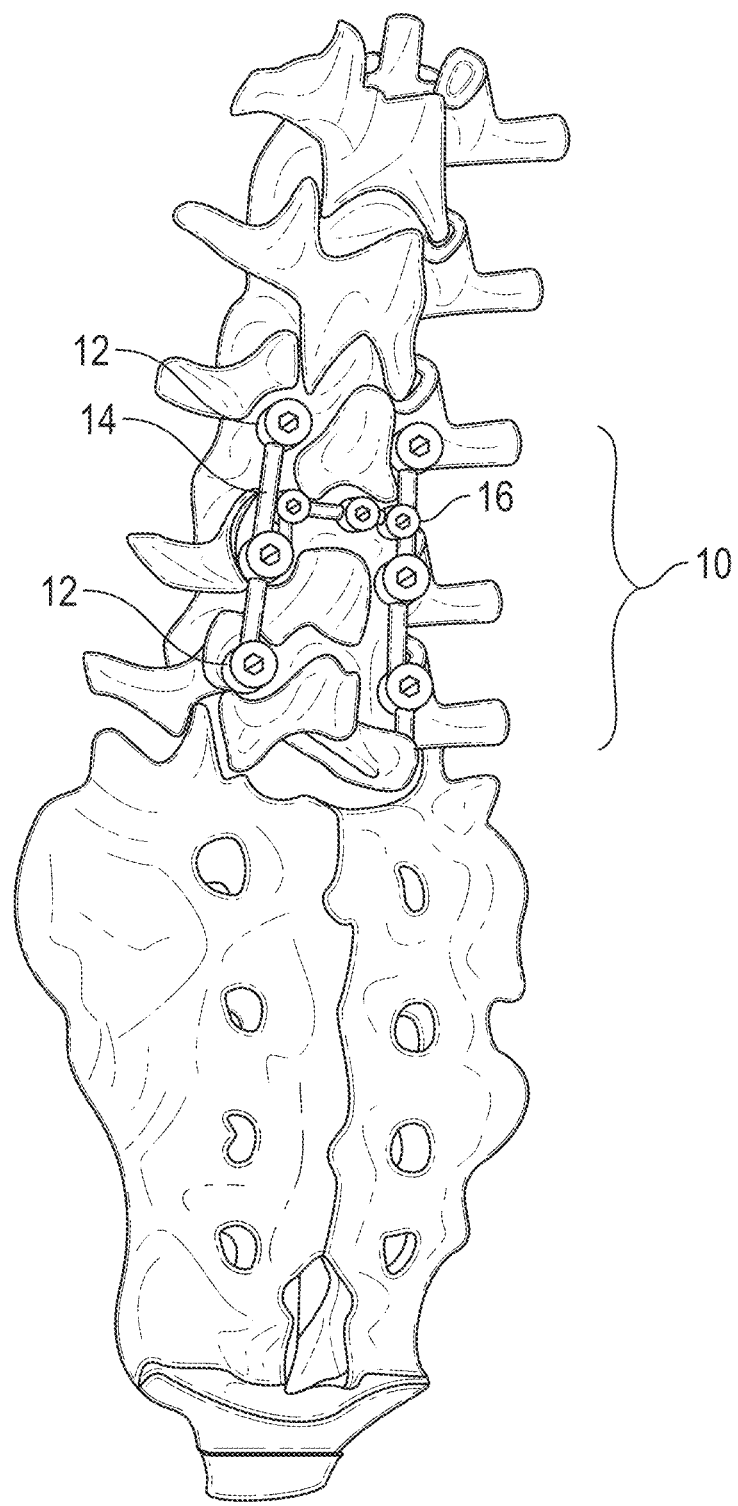
FIG. 1 illustrates a prior art pedicle screw system.

Posterior fixation constructs, comprised of implants including screws, rods, plates, rivets, nuts, bolts, set screws, connectors, etc., can be used to provide fixation for spinal anatomy during corrective techniques. Spine surgeons often perform spine surgery to relieve symptoms associated with degenerative disc disease, spinal deformity, scoliosis, or trauma, among other reasons. In spinal surgery, surgeons attempt to correct deformities, align vertebral bodies, and/or decompress the spinal cord and nerves.

Present posterior fixation device constructs are typically comprised of bone anchors (alternatively, polyaxial bone screws or pedicle screws), circular cross-section rods, and connectors. The variable position of the heads of the polyaxial screws allow for a range of special relationships between the rod and bone screws while still allowing connection between each other. There are several current issues with posterior fixation constructs including the inability to seat the rod within each of polyaxial screw bodies. In these instances, reduction techniques and instruments are used to forcibly deliver the rod the polyaxial head. As reduction force is delivered to the construct, the relationship between polyaxial screws and connected vertebral bodies becomes unpredictable. In some instances, the force delivered to the construct during surgery can cause problems, including bone screw dislodgment from the vertebral body (screw pullout) or implant fractures.

Typically, the surgeon must deliver anchors (e.g., pedicle screws, other bone screws, clips, etc.) to the vertebral bodies. Surgeons must determine a start-point, trajectory, and anchor length and anchor diameter intraoperatively. The surgeon exposes the bone in order to identify an appropriate anatomical start-point and trajectory for the pedicle screw. Using fluoroscopy, the surgeon delivers the anchor to the bone, taking care not to breach the pedicle or vertebral body. This technique exposes the patient, surgeon, and operating room staff to unnecessary radiation. In some instances, delivery of the pedicle screw results in a breach of the cortex and impingement of the nerves by the bone screw. Surgical planning (using radiographic images taken prior to surgery to determine the bone screw's start-point, trajectory, length, and shank diameter) can be used to reduce or eliminate intra-operative radiation associated with fluoroscopy. Prior to implantation the anatomy can be virtually corrected using planning software.

In deformity and degenerative surgeries, correction of malpositioned anatomy is desired. In some cases, only a partial correction is possible, but is worth achieving. In other cases, full correction is possible. One area of frustration for surgeons during delivery of a posterior fixation construct is bending the longitudinal elements (rods) and delivering and securing them to the fixation anchors (bone screws). In the present state, surgeons approximate the desired shape of the rod based on an estimate of the correction to be delivered to the patient. There is no tool or method to determine the optimal degree of correction required and the amount and degree of curvature or bends that need to be placed upon the rod. The rod bending and implantation often occurs at the end of the surgery, following the delivery of the bone screws and the associated receivers of the rod (screw head, etc.). Because this activity occurs at the end of the surgery, the surgeon may be fatigued, stressed, rushed, or otherwise operating with sub-optimal attention or energy. This critical portion of the procedure is what ultimately determines the relationship between vertebral bodies, the decompression of neural elements, and ultimate alignment of anatomy.

One objective of spine surgery is correction of a spinal deformity or re-alignment of vertebral bodies. Current practices require the surgeon to use intra-operative imaging and manipulation of implants that are fixed to the anatomy to adjust relationships between vertebral bodies to correct malalignment. The imaging tools available to the surgeon intraoperatively use radiation to assess relative position of the interested anatomy. It would be beneficial to have a tool and method to plan the surgery and determine (1) the position of implants within anatomy, (2) position of implants relative to other implants, and (3) position of vertebral bodies relative to other vertebral bodies.

These tools and methods disclosed allow the surgeon to perform a virtual surgery on a computer, tablet, smart phone, or other smart device. By planning the surgery prior to the operation, the surgeon can determine the proper three-dimensional alignment before the patient is surgically opened and/or in place on the operating room table. Pre-planning can eliminate some of the intraoperative decision making that takes valuable time while the patient is under sedation or anesthesia, and while the patient is exposed to infection in the operating room, for example with one or more open surgical incisions. Additionally, surgical planning tools and methods can help determine the proper implant selection, including but not limited to the style of implant, the model of implant, the material(s) of the implant, the quantities of implants, or the size parameters (length, width, depth, diameter, etc.) of the implant.

The systems and methods described herein may be utilized to correct other physiological ailments requiring patient-specific implants. For example, wedge-shaped implants for maintaining wedge osteotomies in the spine, or other orthopedic areas such as the hip, jaw, chin or knee for arthritic or non-arthritic conditions, may be designed with the teachings of the present disclosure. Particular procedures include: high tibial osteotomy (tibia), distal femoral osteotomy (femur), Evans wedge or Cotton wedge (foot and ankle).

FIG. 1 illustrates a posterior fixation construct 10 positioned within the lumbar spine. Polyaxial pedicle screws 12 are inserted into the vertebral body through pedicles. The start-point, trajectory, screw length, and diameter (e.g., shank diameter) are determined by the surgeon during surgery using fluoroscopic imaging. Longitudinal elements 14 (e.g., rods) are used to connect screws 12 in a particular relationship to each other, and thus, to maintain two or more vertebrae in a particular relationship to each other. Longitudinal element 14 may be rods, plates, or another type of geometry. In some constructs, connectors 16, are used to provide stabilization or connect elements of the construct. The connector 16 may connect a rod to another rod, or a screw to another screw, or a rod to a screw, or a rod to a portion of bone, or other combinations.

Figure 2:
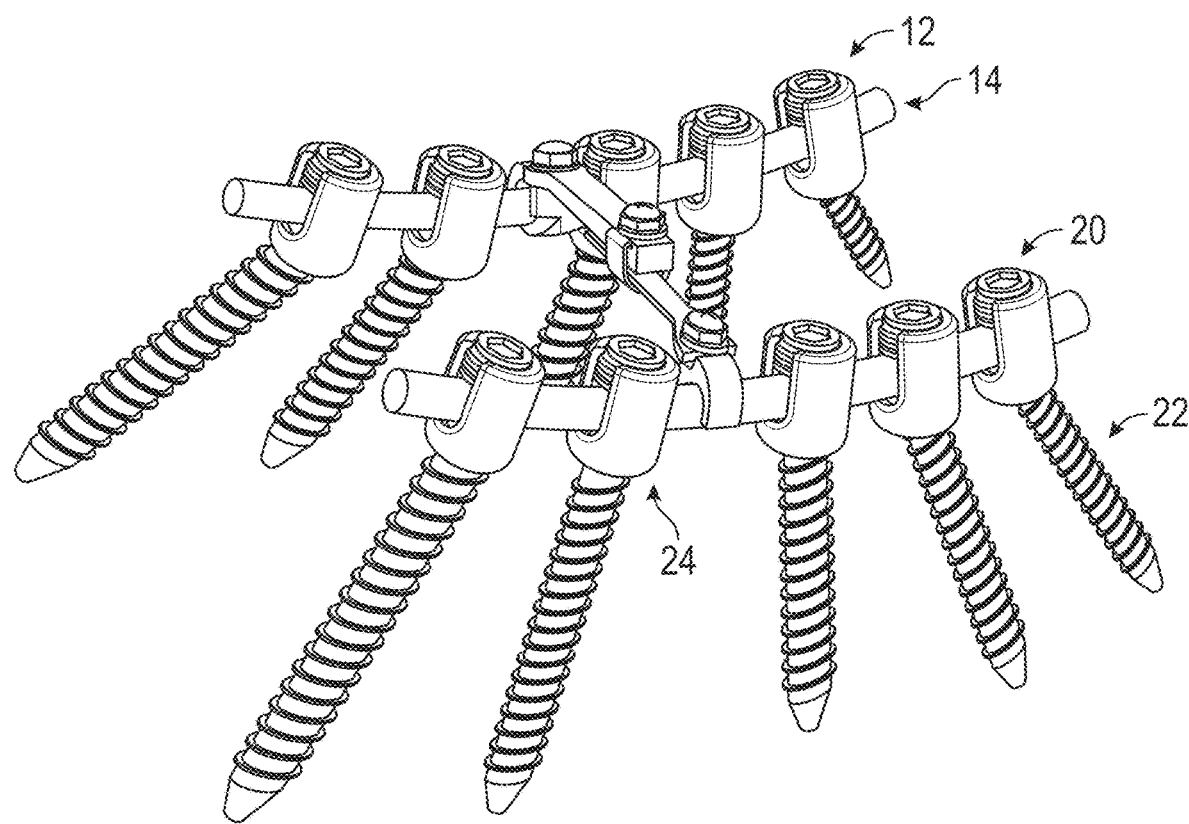
FIG. 2 illustrates the typical components of a pedicle screw system.

FIG. 2 illustrates a common posterior fixation construct. Polyaxial pedicle screws 12 typically have several components. Bone screw shank 22 is used to connect the polyaxial screw 12 to the bony anatomy. Polyaxial screw body 24 is typically coupled to the shank 22 using a spherical mechanism the allows the shank 22 to articulate relative to body 24. This allows body 24 to be positioned to receive rod 14. The screw body 24 may then be tightened to a static relationship with the shank 22. Set screw 20 is used to secure rod 14 into body 24. The set screw 20 may also be used to fix the relationship between the screw body 24 and the screw shank 22, or another element may accomplish this task.

Figure 3:
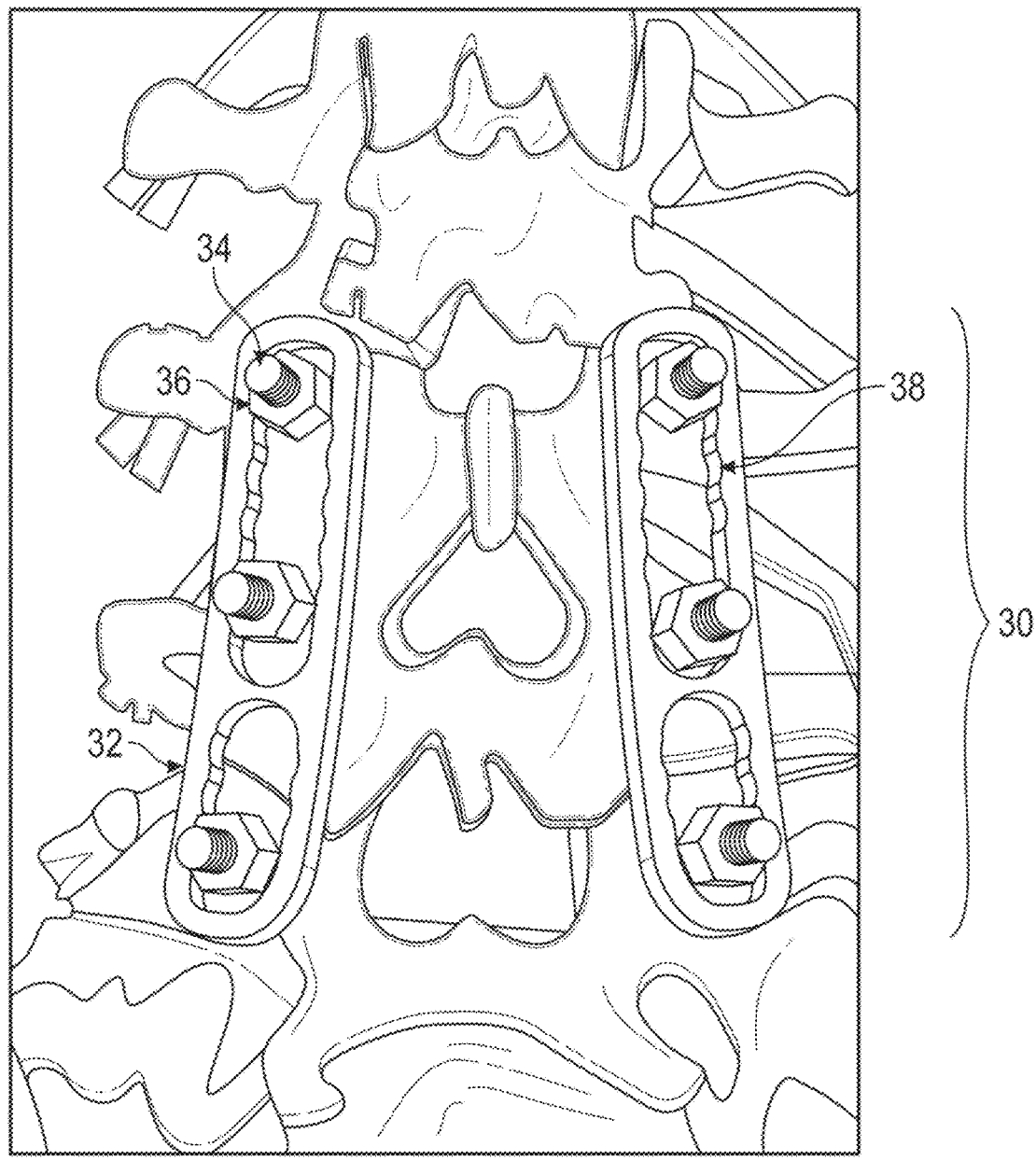
FIG. 3 illustrates a prior art posterior plate fixation system including components such as anatomical (pedicle) screws, bolts, nuts, washers, and plates.

FIG. 3 illustrates a plate type of posterior fixation construct 30. This construct 30 uses bone screws 34 affixed to the vertebral bodies. Plate 32 is used to connect bone screws 34 and provide a mechanism to secure the relationship between bone screws 34 and the attached anatomy. Plate 32 has features 38 designed to secure plate 32 to screw 34. Nut 36 is threaded about screw 34 and used to secure screw 34 to plate 32.

Figure 4:
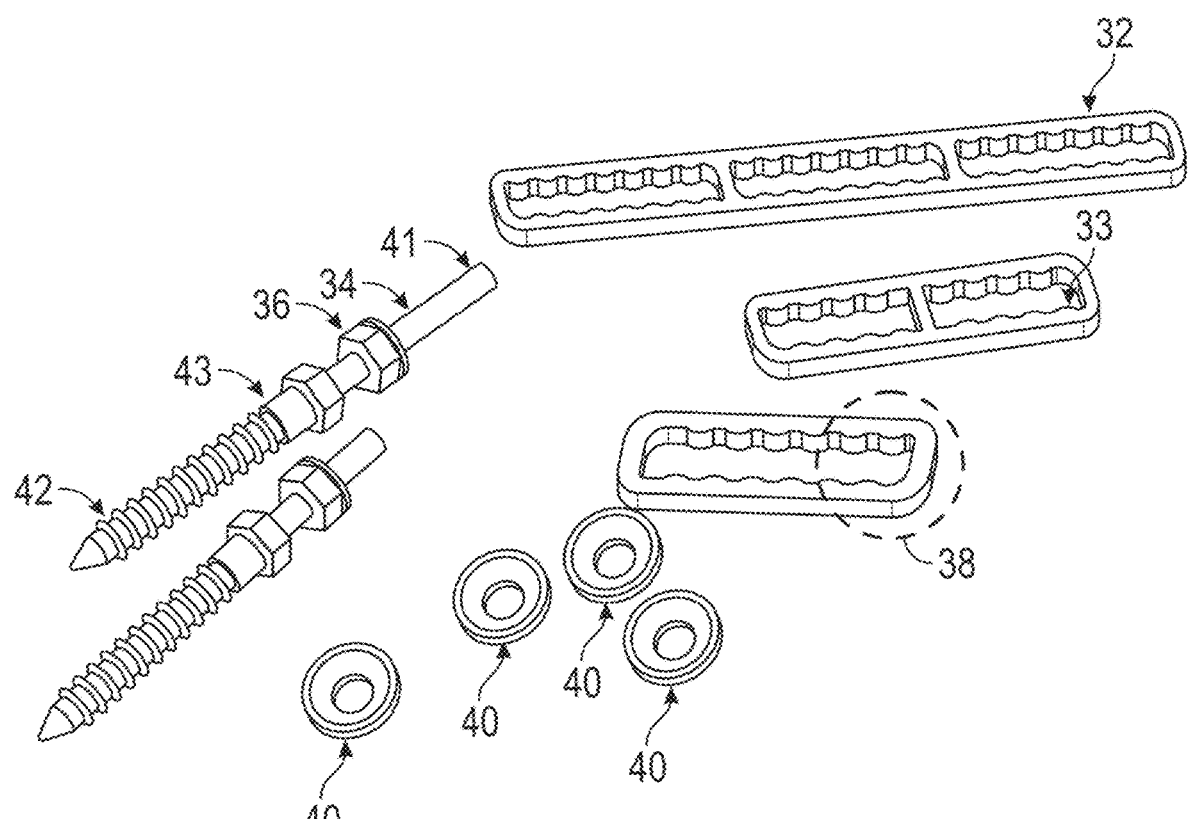
FIG. 4 illustrates the typical features of a posterior plate fixation system.

FIG. 4 illustrates several components of a posterior fixation construct 30. Screw 34 has two threaded portions, the bone screw thread shank 42 and machine screw thread proximal post 41. Bone screw thread shank 42 is delivered to the vertebral body through the pedicle and provides fixation to the anatomy. Machine thread 41 provides a mechanism to deliver fastening nut 36. Nut 36 secures plate 32 to bone screw 34. Washers 40 can be used to provide spacing (angular, axial, etc.) between screw 34, plate 32, and nut 36. Features 38 provide a recess for nut 36 to reside after delivering compression to plate 32. When constructed, plate 32 sits on top of the shoulder 43 of bone screw 34. Plate 32 has slots 33 that allow for machine threaded post 41 to pass though. Nut 36 is threaded on to post 41 to secure plate 32 to screw 34 by compressing plate 32 between nut 36 and shoulder 43.

Figure 5:
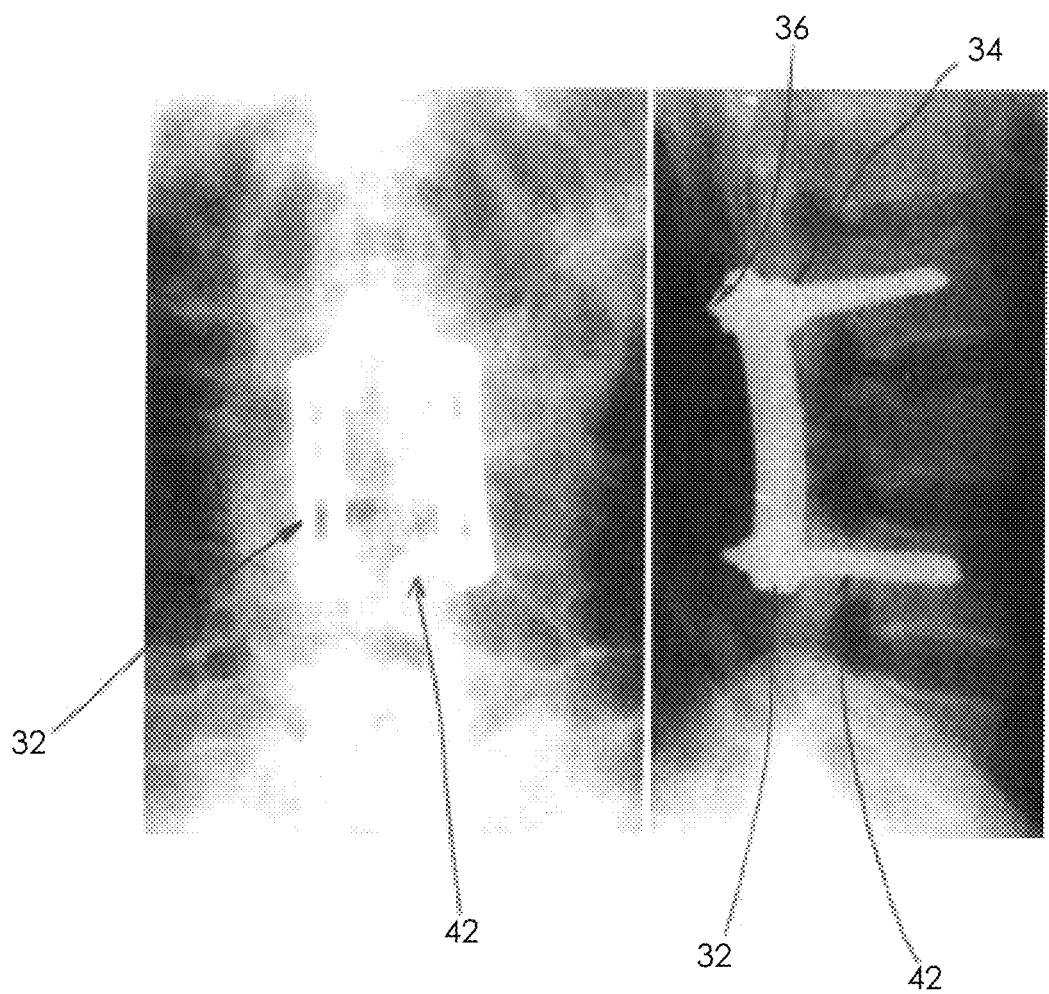
FIG. 5 illustrates the anatomy and placement of a posterior plate fixation system.

FIG. 5 illustrates a posterior fixation construct and associated anatomy when view on a radiograph. In this image, plates 32 and screws 34 are visible. Also shown are bone screw thread shank 42 and nut 36.

Figure 6:
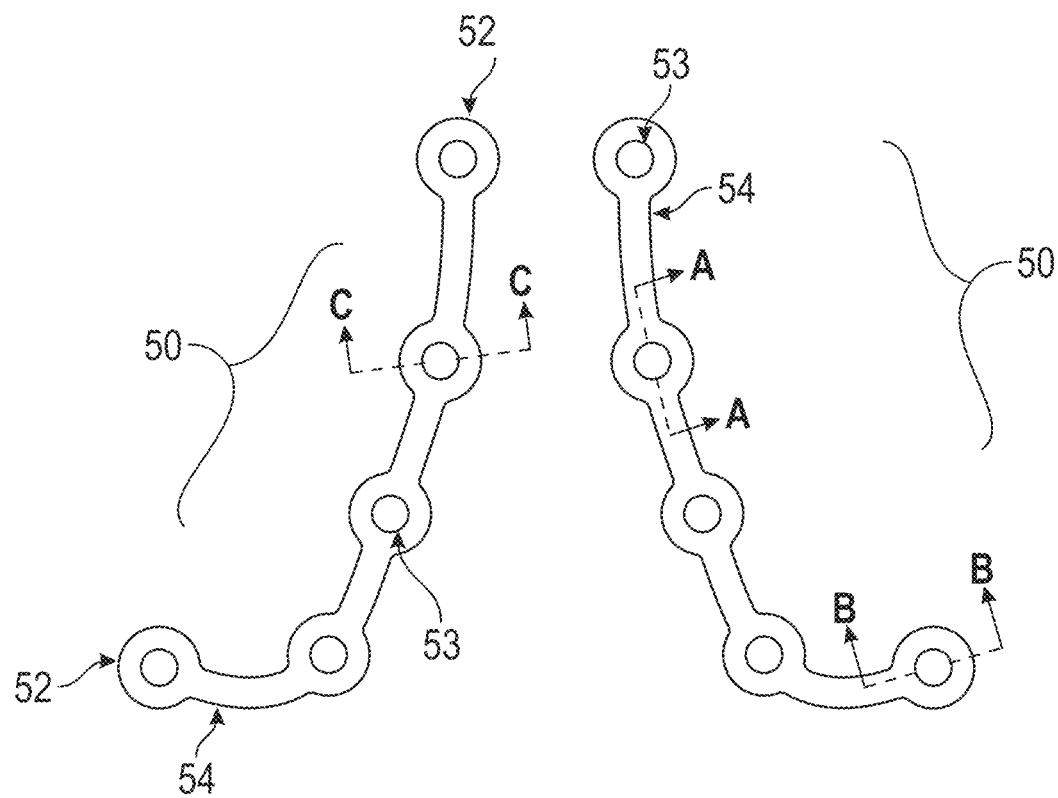
FIG. 6 illustrates a posterior fixation system according to an embodiment of the present disclosure.
Figure 6A:
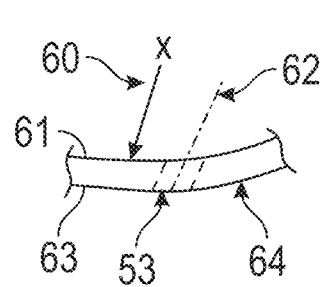
FIG. 6A illustrates a cross-sectional view taken along line A-A of FIG. 6.

FIG. 6 illustrates an embodiment of the present invention. Fixation plate 50 is comprised of longitudinal segments 54 and nodes 52. Nodes 52 have features that provide for receiving of a fixation element or bone screw. Length, orientation, and shape of plate 50, longitudinal segments 54, and nodes 52 can be determined by using surgical planning software.

In one embodiment, the features are a hole 53 that allows for receiving of a bone screw. Holes 53 may be oriented orthogonal to a top or bottom surface. Alternatively, hole axis 62 may be oriented at an angle relative to a top or bottom surface (e.g., oriented at a non-orthogonal angle).

Figure 6B:
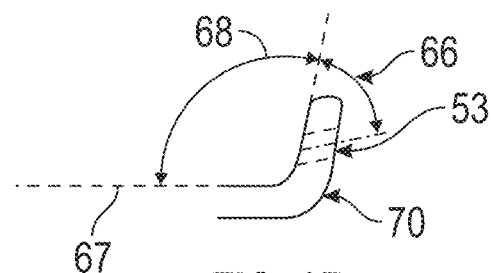
FIG. 6B illustrates a cross-sectional view taken along line B-B of FIG. 6.
Figure 6C:
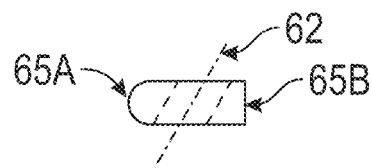
FIG. 6C illustrates a cross-sectional view taken along line C-C of FIG. 6.

Top surface 61 and/or bottom surface 63 may be curved or described by a radius 60. Top surface 61 is shown in FIG. 6 to be concave and bottom surface 63 is shown as convex, but in other embodiments, bottom surface 63 may be concave and top surface 61 may be convex. In still other embodiments one or both of top surface 61 and bottom surface 63 may include one or more convex portion and one or more concave portion. Top and bottom surfaces 61, 63 may be configured with features to provide improved locking between adjacent components (e.g., mating features including teeth, bumps, recesses). Top and bottom surfaces 61, 63 may have a unique shape with features 64 that provide for accommodation of anatomical features. Top and bottom surfaces 61, 63 may be angled relative to one another. Angle 68, angle 66, or arc 70 (FIG. 6B), can be used to describe relationships between sections of top and bottom surfaces 61, 63. In some instances, node 52 can be positioned directly lateral to adjacent node 52. Longitudinal segment 54 may be curved in three dimensions in order to locate node 52 in the optimal position over anatomical features. FIG. 6B shows a terminal node that could be located in an optimal location for an iliac bone anchor. The angle of the hole 53, as shown in FIG. 6B, can be angularly offset (e.g., non-parallel) from the primary plane 67 of plate 50. Medial and lateral surfaces 65 shown in FIG. 6C can be described as flat or contoured to fit anatomy or provide location for graft material. Surface 65A is shown in FIG. 6C as flat, and surface 65B is shown as contoured. Shape and topography of plate 50, nodes 52, holes 53, and longitudinal element 54 can be determined using surgical planning and design software. The plate 60 may comprise multi-planar curves, twists, variable thicknesses, multiple sections of differing density, multiple sections of differing porosity, or multiple sections of differing flexibility/stiffness.

Figure 7:
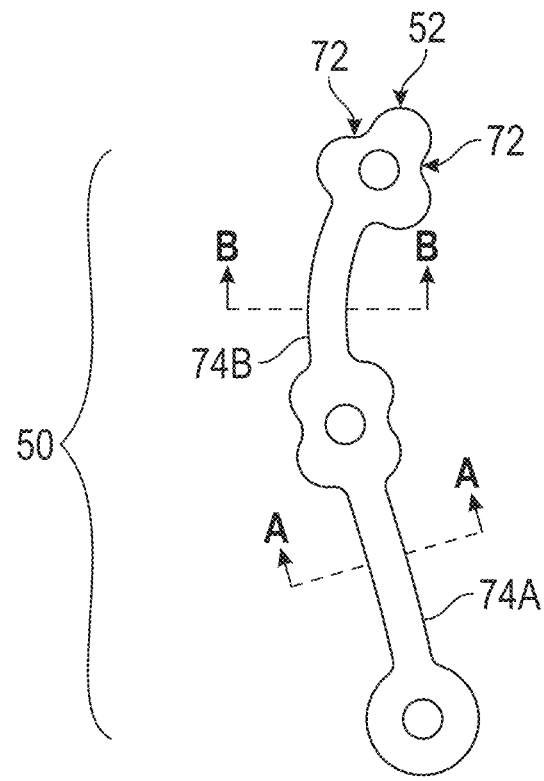
FIG. 7 illustrates components and features of the posterior fixation system according to an embodiment of the present disclosure.
Figure 7A:
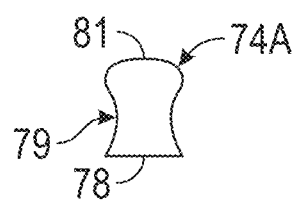
FIG. 7A illustrates a cross-sectional view taken along line A-A of FIG. 7.
Figure 7B:
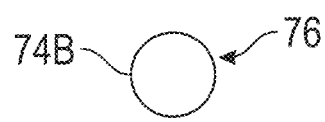
FIG. 7B illustrates a cross-sectional view taken along line B-B of FIG. 7.

FIG. 7 illustrates another embodiment of fixation plate 50. In one embodiment, node 52 can have features 72 to provide for seating against or around anatomy. When viewed in cross-section, longitudinal element 74A, 74B can have variable shapes to provide for mechanical performance or anatomical placement. Feature 79 comprising a concavity can be provided to allow for anatomical placement or mechanical performance. Surface 81 comprising a convexity can be provided to allow for anatomical placement or mechanical performance. Surface 78 can be textured to provide for anatomical placement or mechanical performance. In one embodiment, surface 78 can be roughened to provide for temporary fixation on the adjacent anatomy. Furthermore, surface 78 can be conditioned to encourage or discourage biological reactions. Surface 78 can be impregnated with biological agents to encourage bone growth and/or discourage bacterial growth. In one embodiment, cross-section 76 may be circular in shape. Thus, longitudinal elements 74 may either have similar cross-sectional profiles, or may have two or more different cross-sectional profiles.

Figure 8:
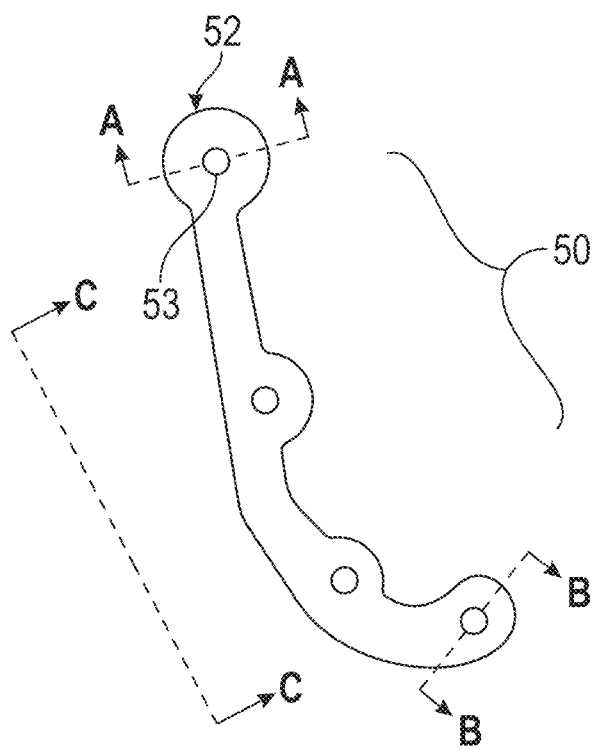
FIG. 8 illustrates features of a system plate and nodes according to an embodiment of the present disclosure.
Figure 8A:
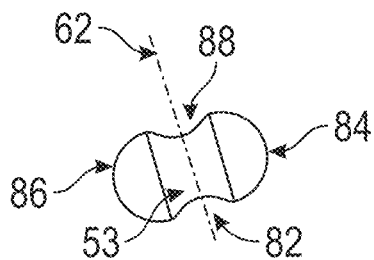
FIG. 8A illustrates a cross-sectional view taken along line A-A of FIG. 8.
Figure 8B:
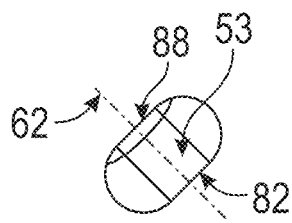
FIG. 8B illustrates a cross-sectional view taken along line B-B of FIG. 8.

FIG. 8 illustrates another embodiment of fixation plate 50. Cross-section of nodes 52 are shown in FIGS. 8A and 8B. In one embodiment, nodes 52 contain holes 53 to provide for bone screws or another anatomical fixation element. Holes 53 may contain features 88 (e.g., teeth, grooves, bosses, keys, recesses, etc.) to allow for seating of a fastener and to provide secure relationship or lock between plate 50, bone screw, and anatomy. Hole 53 can have a central axis 62 to provide communication between top and bottom surfaces. Nodes 52 may have top and bottom surfaces with features 82 to provide for anatomical placement or mechanical performance. Medial and lateral surfaces 84, 86 can be configured to provide for anatomical placement or mechanical performance.

Figure 8C:
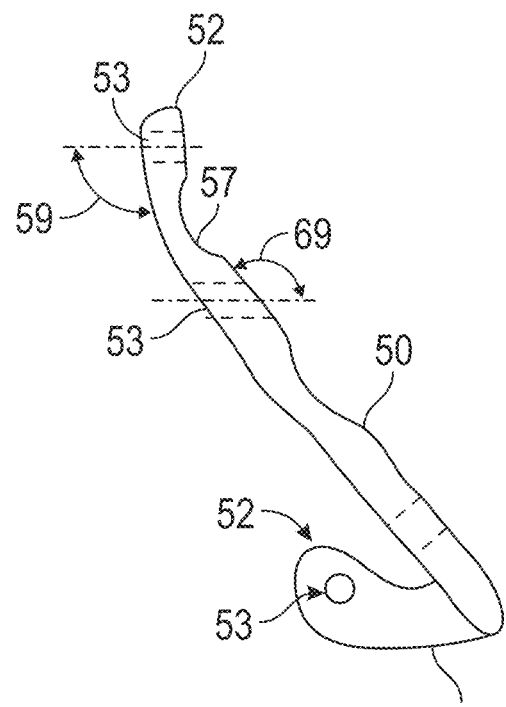
FIG. 8C illustrates a cross-sectional view taken along line C-C of FIG. 8.

FIG. 8C shows another view of plate 50 and highlights the three-dimensionality of plate 50. Lower arm 55 of plate 50 is shown to be out-of-plane relative to the upper section 57. This out-of-plane nature can be applied in relation to the upper section 57 as a curvature representing or matching lordosis, kyphosis, or medial/lateral twisting in a target patient. In this embodiment, angles 59, 69 and radii of curvature can be used to describe the relationship between holes 53 and surface of plate 50. Nodes 52 may include different features, surfaces (e.g. medial vs. lateral, anterior vs. posterior), different hole locations and angulations, and multiple axes. Longitudinal segments 54 may vary in shape, length, or angulation. In some embodiments, portions of the plate 50 are not within the same plane as each other. In some embodiments, the plate 50 is asymmetric. In some embodiments, the asymmetry may be in relation to a longitudinal axis.

Figures 9, 9A:
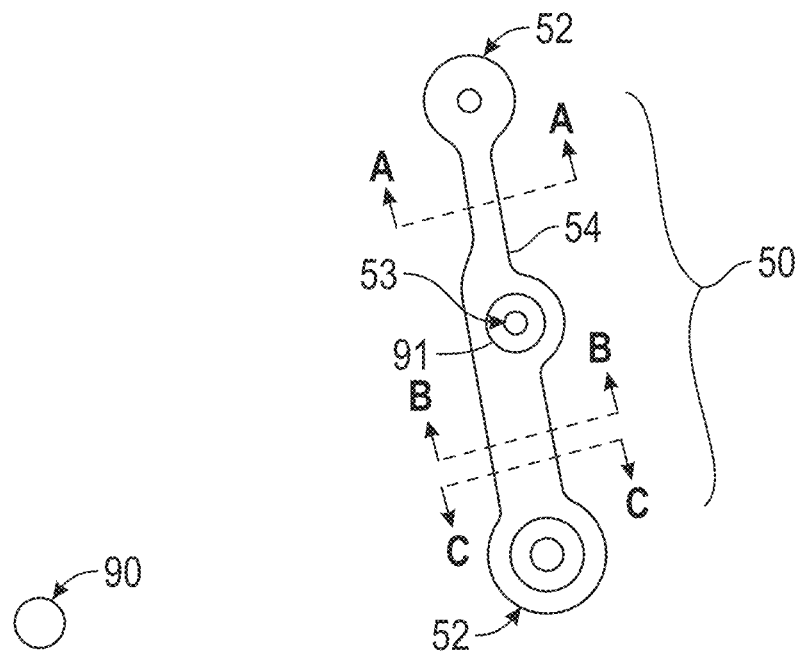
FIG. 9 illustrates features of a longitudinal element according to an embodiment of the present disclosure.
FIG. 9A illustrates a cross-sectional view taken along line A-A of FIG. 9.
Figure 9B:
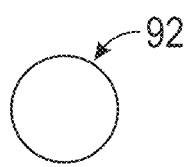
FIG. 9B illustrates a cross-sectional view taken along line B-B of FIG. 9.
Figure 9C:
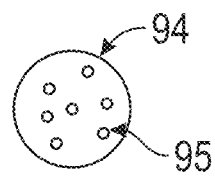
FIG. 9C illustrates a cross-sectional view taken along line C-C of FIG. 9.

FIG. 9 illustrates another embodiment of plate 50. Cross-sectional views in FIGS. 9A, 9B, and 9C show that the size and density of longitudinal elements 54 can be varied. Mechanical performance, such as flexibility or stiffness, can be optimized by changing the shape and composition of longitudinal elements 54. Furthermore, longitudinal elements can be manufactured with a porosity to provide optimized mechanical performance or biological response. Pores 95 can be sized to encourage biological response (e.g., adhesion) or to control/optimize flexibility, or even to increase durability or fatigue strength. The plate 50 may in alternative embodiments receive surface treatment to optimize biological response at the surface. First diameter 90 (FIG. 9A) may be smaller than second diameter 92 or third diameter 94. Feature 91 is configured for locking the plate 50 to a nut 36 or to a locking element 113 (FIG. 10).

Additive manufacturing techniques such as laser sintering or electronic beam fusion can be used to build complex non-planar plates 50 with features to provide for anatomic seating or mechanical performance. Internal geometry particular to additive manufacturing, such as lattice, struts, or weaves may be used to create the preferred embodiment. Additive manufacturing techniques may include, but are not limited to: three-dimensional printing, stereolithography (SLA), selective laser melting (SLM), powder bed printing (PP), selective laser sintering (SLS), selective heat sintering (SHM), fused deposition modeling (FDM), direct metal laser sintering (DMLS), laminated object manufacturing (LOM), thermoplastic printing, direct material deposition (DMD), digital light processing (DLP), inkjet photo resin machining, and electron beam melting (EBM). Additive manufacturing techniques may be used in some embodiments to create a particular matrix of material/void patterns or a particular series of internal support structures of the material, thus controlling stiffness or flexibility, or the proclivity for the implant to ben in one direction more than another (e.g., more flexible along an X-Y plane than along an X-Z planet, etc.

Figure 10:
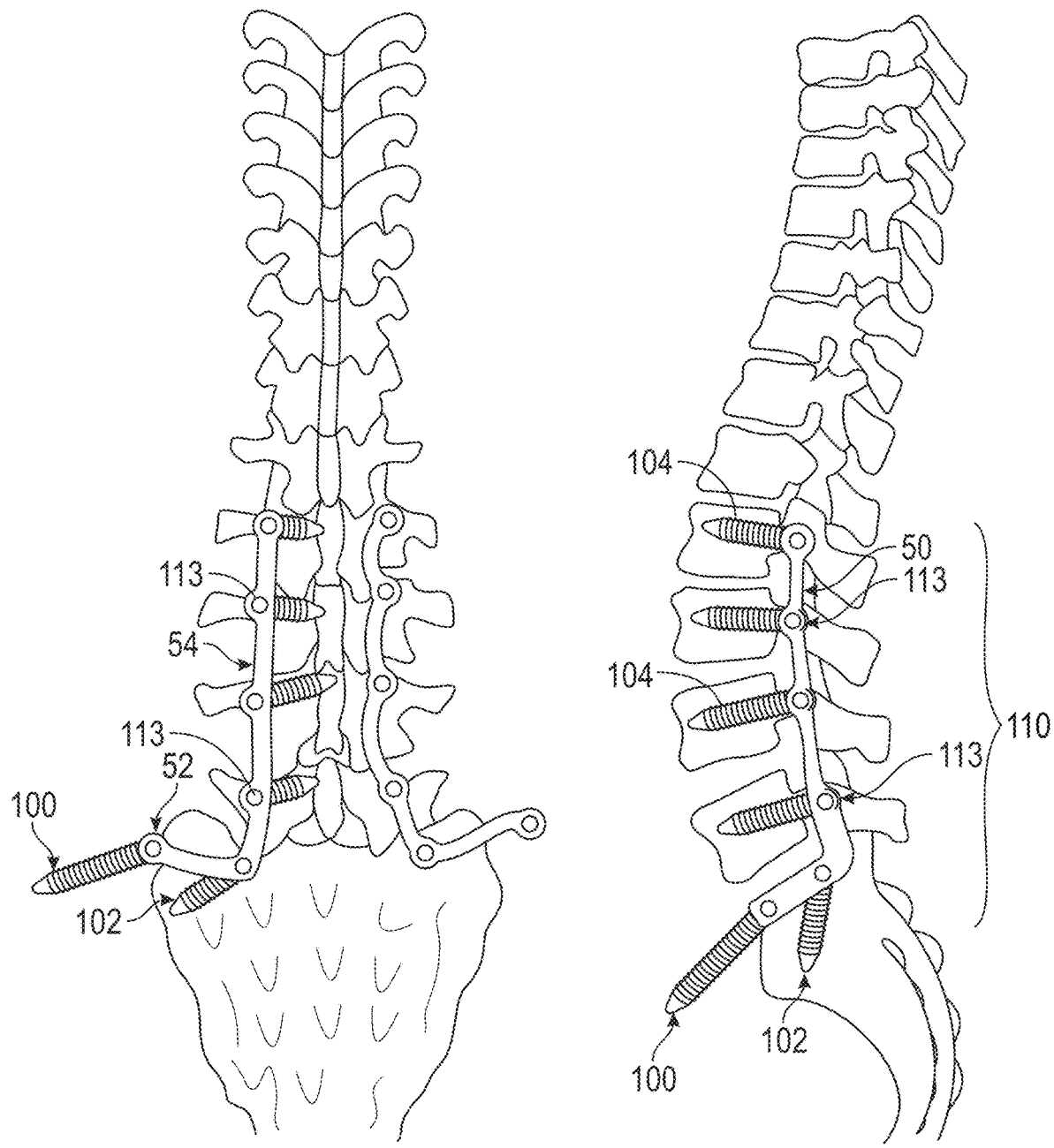
FIG. 10 illustrates the anatomy and placement of a posterior fixation system according to an embodiment of the present disclosure.

FIG. 10 illustrates a plate 50 that has been placed in the lumbar spine. Construct 110 can be used to treat patients who have a degenerative or deformative condition of the spine. In one embodiment, plate 50 is fixed to the spine using bone screws 100, 102, 104. Plate 50 can be designed to accommodate anatomy. Unique shapes or configurations of plate 50 can accommodate individual patient anatomy or mechanical performance. Plate 50 can additionally, or alternatively be configured to provide fixation to the sacrum and/or ilium. Sacral screw 102 and iliac screw 100 can provide fixation to areas outside of the spine. Surgeons using traditional fixation devices (rods, screws, connectors, etc.) recognize that bending a rod to the appropriate shape for iliac fixation is difficult and often results in the use of supplemental devices that are difficult to use.

Locking element 113 is configured to secure bone screw 100, 102, 104 to plate 50. Longitudinal element 54 can be configured to (1) avoid anatomy (e.g., have a particular shape), (2) engage anatomy (e.g., grasp a particular landmark or feature, including a process or lamina) (3) have a desired mechanical performance (e.g., have particular dimensions or shape), or (4) provide a biological response (e.g., have a particular surface configuration or a particular coating). In one embodiment, locking element 113 can be configured to provide limited relative movement between bone screw 100, 102, 104 to encourage fusion or avoid causing or worsening adjacent segment disease (proximal junctional kyphosis). In one embodiment, locking element 113 acts to expand a spherical feature on the proximal end of bone anchor 100, 102, 104. In one embodiment, locking element 113 and longitudinal element 54 can be configured to have mating features that constrict or control relative motion between components. Mating features can include teeth, grooves, bosses, reliefs, and surface finishes to allow for interdigitation and mechanical engagement between components.

Figure 11:
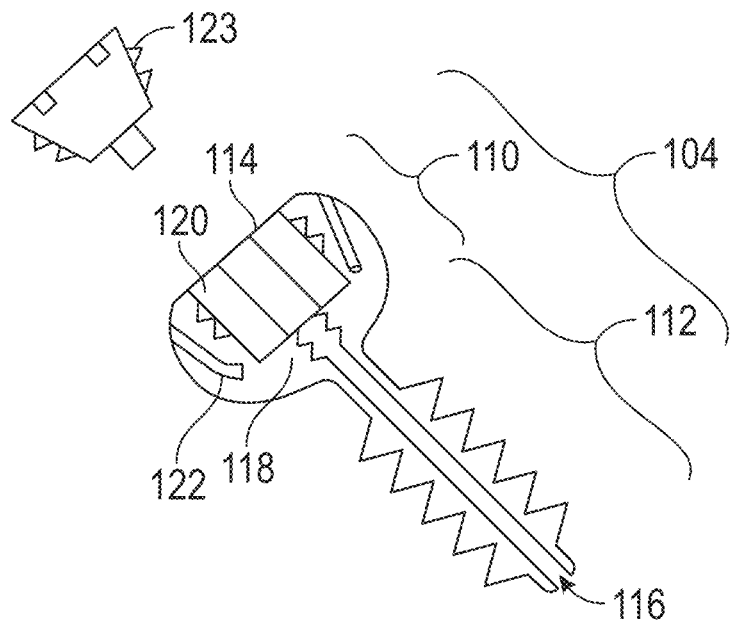
FIG. 11 illustrates a bone anchor and associated features according to an embodiment of the present disclosure.

FIG. 11 illustrates a bone anchor 104 and associated features. Proximal head 110 of bone anchor 104 can be spherical in shape to allow for variable angular position relative to plate 50. Bone anchor shank 112 is configured to provide fixation to bony anatomy. In this embodiment, shank 112 is threaded and includes a cannulation 116 to facilitate implantation. In select spinal surgeries (percutaneous or minimally invasive), k-wires can be used to prepare a trajectory and depth for the bone anchor. The anchor 104 can be delivered over the wire to anatomy, with the wire extending through the cannulation 116. Drive feature 114 is used to drive anchor 104 into bone and can be configured as hexagonal in shape, for interfacing with a mating hexagonal driving element (screwdriver, etc.).

Bone anchor 104 has a proximal head 110 that may have slits 122 to allow expansion (e.g., radial expansion) of proximal head 110. As tapered plug 123 is delivered to head 110, for example, by rotational threading, it causes expansion of head 110. Internal threads 118, 120 can be used to engage and retain plug 123 that is delivered to the head after final seating within plate 50.

Figure 12:
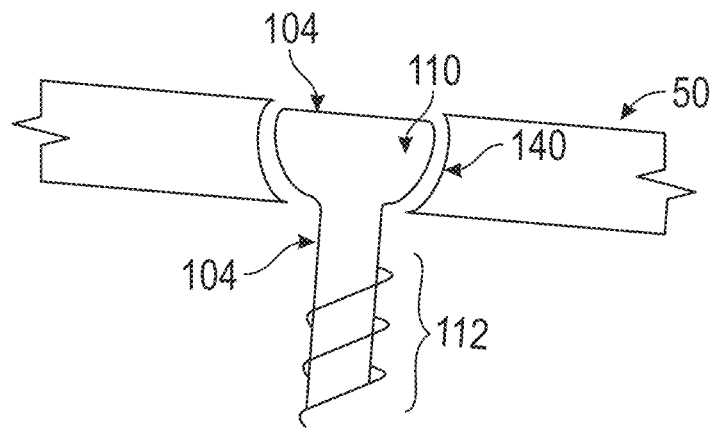
FIG. 12 illustrates a bone anchor and plate interface according to an embodiment of the present disclosure.

FIG. 12 illustrates a bone anchor 104 and plate 50 interface. Proximal head 110 can be spherical in nature and be configured to fit and be contained within pocket 140 of plate 50. In one embodiment, pocket 140 can be spherical in nature.

Figure 13:
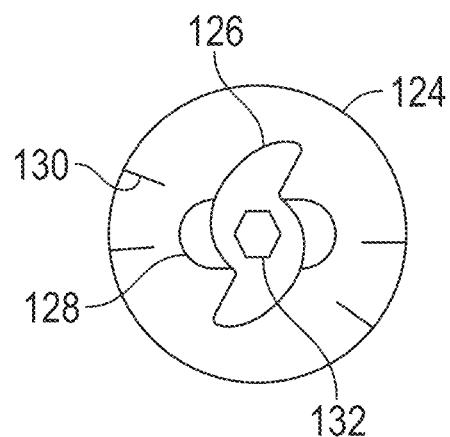
FIG. 13 illustrates proximal features of a bone anchor according to an embodiment of the present disclosure.

FIG. 13 illustrates proximal features of a bone anchor 104. Proximal head 124 can be configured to contain features that to allow expansion of head 124 into pocket 140 (FIG. 12) to fix the relationship between bone anchor 104 and plate 50. In one embodiment, cam 126 can be configured to expand head 124 upon rotation of cam 126 using drive feature 132 (e.g., driven by screwdriver, etc.). Profiled relief 128 can be configured to provide expansion of head 124 after final seating within plate 50. In one embodiment, rotation of cam 126 causes contact between cam 126 and head 124, and as cam 126 contacts profiled relief 128, it causes expansion of the head 124. Slits 130 interrupt the circumferential continuity of the head 124 and allow head 124 to expand (e.g., radially) and fix the relationship between anchor 104 and plate 50.

Figure 14:
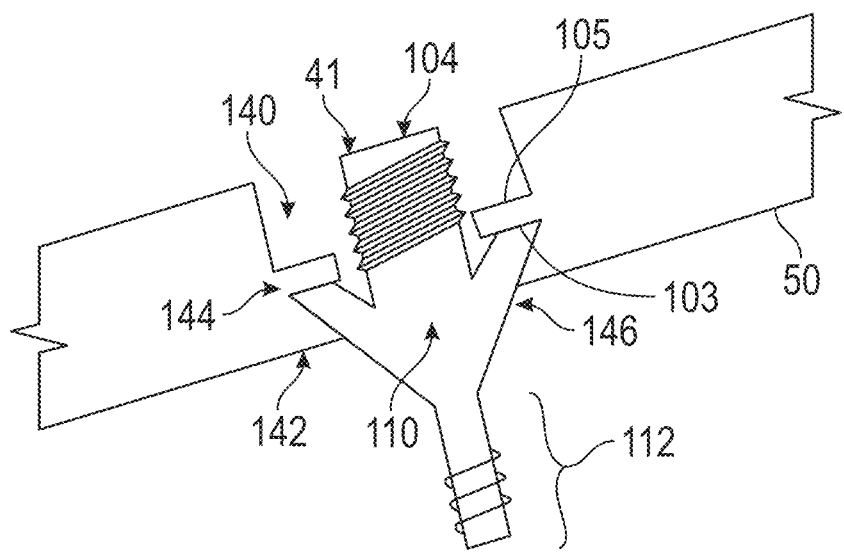
FIG. 14 illustrates a bone anchor and plate interface according to an embodiment of the present disclosure.

FIG. 14 illustrates a bone anchor 104 and plate interface. Proximal head 110 and pocket 140 can contain several features to help secure anchor 104 to plate 50. In one embodiment, threads 41 are present on the external surface of the proximal head 110. As shown in FIG. 14, head 110, can be configured to have an arm 146 that can flex. Arm 146 extends proximally and radially simultaneously, and thus is swept-back angularly in relation to a longitudinal axis of the anchor 104. When inserting anchor 104 through plate 50 and into bone, the arm 146 can flex inwardly to allow it to pass shoulder 144. The arm 146 is shown in FIG. 14 in a position after it has passed the shoulder 144. Once past the shoulder 144, the arm 146 can be used to brace anchor against plate 50. The arm 146 is shown in FIG. 14 applying a normal force against an inner surface 103 of the shoulder 144. The arm 146 extends past the bottom surface 142 of the plate 50, to the shank 112. In other embodiments, the arm 146 may remain between the two opposing surfaces of the plate 50. Proximal head threads 41 can be used to secure anchor 104 and plate 50 (e.g., by screwing a nut, or screwing the locking element 150 of FIG. 15. over the threads 41 such that it contacts the shoulder 144 at an outer surface 105 of the shoulder, opposite the inner surface 103). In one embodiment, the anchor 104 is driven through plate 50 and proximal head 110 into pocket 140 through plate 50. Locking element 150 (FIG. 15) can be configured to be threaded onto tread 41 to lock anchor 104 to plate 50.

Figure 15:
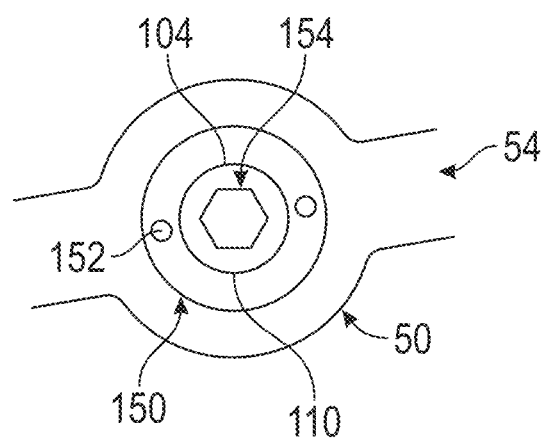
FIG. 15 illustrates proximal features of a bone anchor, plate, and locking element according to an embodiment of the present disclosure.

FIG. 15 illustrates proximal features of a bone anchor 104, plate 50, and locking element features. Shown in FIG. 15 is plate 50, longitudinal element 54, proximal head 110 (of bone anchor 104) containing drive feature 154. Proximal drive feature 154 can be configured as hexagonal in shape and is used (with a driver) to drive anchor 104 through plate 50 and into bony anatomy. In one embodiment, locking element 150 can be threaded and configured to lock plate 50 between anchor 104 and locking element 150. Features 152 on locking element 150 can be used to drive locking element 150 into plate 50 to secure anchor 104 to plate 50.

Plate 50, anchor 100, 102, 104, and locking element 150 and features thereof can be manufactured of materials typical of medical implants, including, but not limited to, titanium, titanium alloy, Ti6Al4V, stainless steel, cobalt chrome, polymers, polyether ether ketone (PEEK), etc. Anchors 100, 102, 104 may alternatively be constructed of rivets, bolts, or other fasteners.

Figure 16:
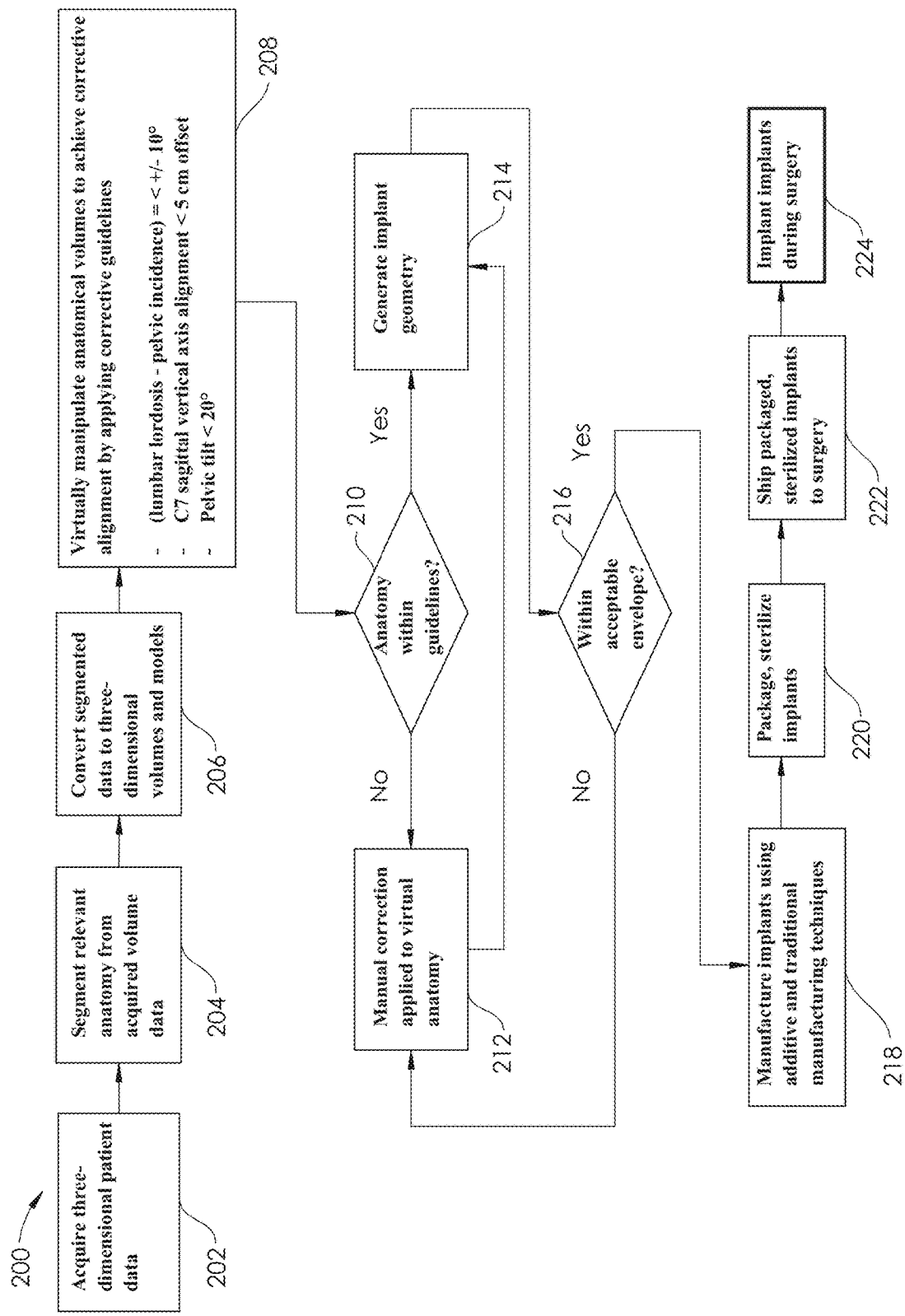
FIG. 16 is a flow chart of a method for producing and utilizing patient-specific implants according to an embodiment of the present disclosure.

FIG. 16 illustrates a method 200 for utilizing a system for producing patient-specific implants. In step 202 three-dimensional scan data of a patient is obtained from a CT, MRI, x-ray, PET or another type of imaging modality. Step 204 segments the scan data into relevant and irrelevant sets. In one embodiment, relevant data set includes bony tissue. Segmentation step 204 can use a thresholding operation, automated filters, machine learning, or artificial intelligence to identify bony tissue based on tissue density and pixel density. The relevant data is then converted into three-dimensional volume and models in step 206. In some cases, the relevant data may correspond to a diseased or deformed portion of the spine, including a particular number of successive vertebrae and the surrounding soft tissue. In some cases, the entire spine may be selected.

A computer may be used for processing and manipulation of this data. For example, the user interface associated with least one computer memory that is not a transitory signal and comprises instructions executable by at least one processor may be utilized to select a region of interest. A system containing the memory may include any number of custom stand-alone devices, or any mobile device, such as an iPhone, smart phone, ipad, tablet, laptop, desktop, or mainframe computer. The system may also be configured to access the memory remotely, for example, via internet browser access or other wireless means. The three-dimensional image can be converted into a form such that is can be manipulated by a user to measure anatomical deformities related to the disease (e.g., spine disease). The information can then be used by a medical professional or technical professional in conjunction or collaboration with a medical professional, to design (reconfigure) the optimized geometry of the corrected spine, thus allowing the design of an implant to treat the particular disease or malady.

In step 208 the computer memory is utilized to apply one or more predictive correction guidelines to the spine or to the selected portion of the spine, or at least a section thereof. A number of predictive correction guidelines may be utilized, but in one embodiment a set of three predictive guidelines are applied, relating to pelvic tilt, sagittal alignment, and lumbar lordosis. The predictive guideline regarding pelvic tilt is can be the equation wherein the pelvic tilt less than 20 degrees. The predictive guideline regarding sagittal vertebral axis (SVA) can be defined by the equation wherein the C7 sagittal vertical axis is not more than 5 cm from the most posterior portion of the superior sacral endplate. The predictive guideline regarding lumbar lordosis 114 is defined by the equation wherein an absolute value of the difference between pelvic incidence and lumbar lordosis less than 10 degrees. Predictive guidelines may be used as described in "Current Surgical Strategies to Restore Proper Sagittal Alignment" by Luiz Pimenta, Journal of Spine, 2015, Volume 4, Number 4, (2 pages), which is incorporated herein by reference in its entirety for all purposes.

In decision point 210, the computer memory is utilized to determine whether, in the current state of the spine provided by the three-dimensional image, the predictive guidelines from step 208 are achieved. If one or more of the predictive guidelines from step 208 are not true for the spine segments selected, then a user may utilize a user interface to adjust the virtual anatomy into a preferred alignment, as shown in step 212. For example, if the pelvic tilt is determined to be 20° or greater, a user may input or toggle an adjustment that changes the amount of correction in order to achieve a pelvic tilt less than 20°. If it is determined that the predictive guidelines are all achieved (whether user adjustment was or was not required), the system generates three-dimensional implant(s) geometry in step 214. The three-dimensional implant(s) geometry may in some cases define a single interbody device, several interbody devices, or posterior fixation plate 50 geometry (including node 52, hole 53, and longitudinal element 54 geometries). In some cases, the three-dimensional geometry may define one or more interbody devices for a single level of the spine, or in other cases may define one or more interbody devices from two or more levels of the spine. In one embodiment, the data creates a point cloud map, which is then converted to multiple interconnected triangles to create a surface mesh. Based on known density discrepancies between bone and tissue, the three-dimensional mesh surface is parsed for bone surface data and converted to a three-dimensional volume. The converted data is saved into memory with a readable file format, such as . STL, .OBJ, or other CAD (computer-aided design) readable file format. In this CAD readable file format, the individual spine vertebral bodies can be isolated and manipulated in the axial, coronal, and sagittal planes.

After the three-dimensional geometry is generated, the system checks in decision point 216 whether the particular correction is within cleared parameters. For example, within a particular amount of correction that is approved under a regulatory clearance; or, within a particular amount of correction that is approved under an IRB-controlled or FDA-controlled clinical trial. Additional to, or instead of, the amount of correction, other parameters may determine whether the three-dimensional geometry performs within cleared parameters in decision point 216. For example, the thickness of longitudinal element 54 or node 52 may be controlled and many not fall below a threshold or the dimensions and density of an interbody device may not exceed a predetermined value. If the correction (or other parameters) is not within the cleared range(s), user-initiated input may be performed, as in step 212. In some embodiments, the system may suggest the amount to adjust each parameter of spine alignment, allowing the user to accept this suggestion, or to choose a different value of change. In some cases, step 212 may not be necessary, for example, when certain procedures do not have implant-based regulatory limitations. A particular manner of validating a cleared amount of correction, is to check the three-dimensional envelope of the spine implant at both the maximum material condition and the least material condition. For example, an FDA clearance may take into account both of these conditions, in one or more patient indications.

Once the three-dimensional geometry is accepted by the user, and, if applicable, by the limitations of step 216, the implant(s) may be manufactured. The patient prescription containing volumes of implant(s) may comprise one or more three-dimensional files that are used in additive manufacturing, including, but not limited to: .AMF, .X3D, Collada (Collaborative Design Activity), .STL, .STP, .STEP, or .OBJ. The patient prescription may alternatively comprise one or more three dimensional files, including, but not limited to: .IGS, .STP, .STEP, .3ds, .blend, .dae, .ipt, ,skp, .fbx, .lwo, .off, .ply., .sldprt, .sldasm, and .X_T. In some cases, the patient prescription may also include one or more two-dimensional files, for example, to map or guide the surgical treatment, or to stage the utilization of each implant. The two-dimensional files may include, but are not limited to: .dwg, .dwf, .dxf, .pdf, or .acis.

The step 218 may include using the three-dimensional files to manufacture the implant(s) using one or more additive manufacturing or subtractive (traditional) manufacturing methods. Additive manufacturing methods include, but are not limited to: three-dimensional printing, stereolithography (SLA), selective laser melting (SLM), powder bed printing (PP), selective laser sintering (SLS), selective heat sintering (SHM), fused deposition modeling (FDM), direct metal laser sintering (DMLS), laminated object manufacturing (LOM), thermoplastic printing, direct material deposition (DMD), digital light processing (DLP), inkjet photo resin machining, and electron beam melting (EBM). Subtractive (traditional) manufacturing methods include, but are not limited to: CNC machining, EDM (electrical discharge machining), grinding, laser cutting, water jet machining, and manual machining (milling, lathe/turning). The additive (or subtractive) manufacturing may be used to construct the plate 50, or the anchors 100, 102, 104, or the locking elements 150.

Following the manufacture of the implant, a bone-friendly scaffold is created for fusion to one or more vertebrae. The implant may comprise one or more of the following materials: titanium, titanium alloy, titanium-6AL-4V, tantalum, and PEEK (polyether ether ketone). The implant may also comprise/be coated with a biologic material. Examples of potential biological materials may include, but are not limited to, hydroxylapetite (hydroxyapetite), recombinant human bone morphogenic proteins (rhBMP-2, rhBMP-7), bioactive glass, beta tri-calcium phosphate, human allograft (cortical and/or cancellous bone), xenograft, other allograft, platelet rich plasma (PRP), stem cells, and other biomaterials. In addition, synthetic ceramics having osteogenic properties may be utilized.

The manufacture of the implant may be further guided by patient information, including patient age, patient weight, BMI, activity level, DEXA score, bone density, or prior patient surgical history. For example, a patient with a high BMI (body mass index) can require a stiffer or stronger implant. The lattice structure forming the implant can be optimized to meet the patient's biomechanical needs for stability. Additionally, a patient with a low BMI and/or with osteoporotic bone or osteopenia (low DEXA score) can benefit from an implant having lower stiffness, thus helping to reduce the risk of poor performance. Furthermore, a patient having a previously failed fusion may be at risk for adjacent level disc disease and/or proximal joint kyphosis. An implant can be tailored to alleviate this particular situation.

The implant is packaged and sterilized in step 220. The implant is shipped in sterile form to the surgical site (operating room of a hospital or surgery center) in step 222. In some embodiments, step 220 may be performed at the site of surgery, thus making step 222 unnecessary. The implant is implanted within a patient in step 224.

The method 200 may be used to simulate and construct any portion or characteristic of the plate 50, including node locations, hole locations, hole angles, longitudinal segment shape, longitudinal segment thickness, or longitudinal segment density. The method 200 may utilize any of the steps and techniques disclosed in co-pending U.S. patent application Ser. No. 16/207,116, filed on Dec. 1, 2018, and entitled "Systems and Methods for Multi-Planar Orthopedic Alignment," which is incorporated by reference in its entirety for all purposes.

The ranges disclosed herein also encompass any and all overlap, sub-ranges, and combinations thereof. Language such as "up to," "at least," "greater than," "less than," "between," and the like includes the number recited. Numbers preceded by a term such as "approximately", "about", and "substantially" as used herein include the recited numbers (e.g., about 10%=10%), and also represent an amount close to the stated amount that still performs a desired function or achieves a desired result. For example, the terms "approximately", "about", and "substantially" may refer to an amount that is within less than 10% of, within less than 5% of, within less than 1% of, within less than 0.1% of, and within less than 0.01% of the stated amount.

While embodiments have been shown and described, various modifications may be made without departing from the scope of the inventive concepts disclosed herein.

What is claimed is:

1. A personalized spinal fixation system comprising:
   a surgical planning software tool configured to (1) generate a three-dimensional virtual model of at least a portion of a subject's spinal anatomy, (2) measure the three-dimensional virtual model to obtain one or more measurements associated with at least one of a pelvic tilt, sagittal alignment, or lumbar lordosis of the subject's spinal anatomy, (3) based at least in part on the obtained one or more measurements, adjust relationships of the subject's spinal anatomy in the virtual model to provide a corrected spinal geometry that at least partially corrects one or more anatomical deformaties of the subject's spinal anatomy, (4) apply one or more predictive guidelines to the virtual model to determine if the corrected spinal anatomy conforms to the one or more predictive guidelines, wherein the predictive tilt, sagittal alignment, or lumbar lordosis, and (5) if the corrected spinal anatomy confroms to the one or more predictive guidelines, at least partially design a plate for achieving the corrected spinal geometry when implanted in the subject;
   at least one bone anchor;
   the plate designed for achieving the corrected spinal geometry, the plate having a shape that does not conform to a single plane and being configured to extend across at least one intervertebral gap when implanted in the subject, wherein the shape of the plate is at least partially determined by the surgical planning software tool, and wherein the plate comprises at least one node having a hole configured to receive the at least one bone anchor; and
   a locking element configured to connect the at least one bone anchor to the plate, wherein the plate is manufactured using additive manufacturing.

2. The fixation system of claim 1, wherein the additive manufacturing is guided by the surgical planning software tool.

3. The fixation system of claim 1, wherein the plate is configured to provide fixation to surgically adjusted spinal anatomy of the subject to achieve the corrected spinal geometry.

4. The fixation system of claim 3, wherein the corrected spinal geometry comprises a partial or complete correction of a deformation.

5. The fixation system of claim 1, wherein each of the bone anchor, the plate, and the locking element is configured to lock with at least one of the others of the bone anchor, the plate, and the locking element.

6. The fixation system of claim 1, wherein the plate contains one or more longitudinal elements configured to connect the at least one node to at least a second node.

7. The fixation system of claim 1, wherein the plate is configured to have a geometry that allows for iliac fixation.

8. The fixation system of claim 1, wherein the plate has a surface treatment to encourage biological response.

9. The fixation system of claim 1, wherein the plate has a variable density.

10. The fixation system of claim 1, wherein the plate has a variable porosity.

11. The fixation system of claim 1, wherein the surgical planning software tool comprises at least one computer memory that is not a transitory signal, the at least one computer memory comprising instructions executable by at least one processor.

12. A personalized spinal fixation system comprising:
   a surgical planning software tool configured to (1) generate a three-dimensional virtual model of at least a portion of a subject's spinal anatomy, (2) measure the three-dimensional virtual model to obtain one or more measurements associated with at least one of a pelvic tilt, sagittal alignment, or lumbar lordosis of the subject'spinal anatomy, (3) based at least in part on the obtained one or more measurements, adjust relationships of the subject's spinal anatomy in the virtual model to provide a corrected spinal geometry that at least partially corrects one or more anatomical deformaties of the subject's spinal anatomy, (4) apply one or more predictive guidelines to the virtual model to determine if the corrected spinal anatomy conforms to the one or more predictive guidelines, wherein the predictive tilt, sagittal alignment, or lumbar lordosis, and (5) if the corrected spinal anatomy confroms to the one or more predictive guidelines, at least partially design a plate for achieving the corrected spinal geometry when implanted in the subject, wherein the implant includes
- a plate having a shape that does not conform to a single plane and being configured to extend across at least one intervertebral gap when implanted in the subject, wherein the shape of the plate is at least partially determined by the surgical planning software tool, and wherein the plate comprises at least one node having a hole configured to receive the at least one bone anchor,
- at least one bone anchor, and
- a locking element configured to connect the at least one bone anchor to the plate.

13. The fixation system of claim 12, wherein the surgical planning software tool is configured to determine a shape and topography of the plate, and wherein the shape and the topography of the plate are designed to mate with the patient's spinal anatomy.

14. The fixation system of claim 12, wherein the implant is configured to provide fixation to surgically adjusted spinal anatomy of the subject to achieve the corrected spinal geometry.

15. The fixation system of claim 12, wherein the surgical planning software tool comprises at least one computer memory that is not a transitory signal, the at least one computer memory comprising instructions executable by at least one processor.

16. A personalized spinal fixation system comprising:
a surgical planning software tool configured to (1) generate a three-dimensional virtual model of at least a portion of a subject's spinal anatomy, (2) measure the three-dimensional virtual model to obtain one or more measurements associated with at least one of a pelvic tilt, sagittal alignment, or lumbar lordosis of the subject's spinal anatomy, (3) based at least in part on the obtained one or more measurements, adjust relationships of the subject's spinal anatomy in the virtual model to provide a corrected spinal geometry that at least partially corrects one or more anatomical deformities of the subject's spinal anatomy, (4) apply one or more predictive guidelines to the virtual model to determine if the corrected spinal anatomy conforms to the one or more predictive guidelines, wherein the predictive guidelines include predetermined values for one or more of pelvic tilt, sagittal alignment, or lumbar lordosis, and (5) if the corrected spinal anatomy conforms to the one or more predictive guidelines, at least partially design an implant for achieving the corrected spinal geometry when implanted in the subject, wherein the implant includes
- a plate having a shape that does not conform to a single plane and being configured to extend across at least one intervertebral gap when implanted in the subject, wherein the shape of the plate is at least partially determined by the surgical planning software tool, and wherein the plate comprises at least one node having a hole configured to receive the at least one bone anchor, and
- at least one bone anchor.

17. The fixation system of claim 16, wherein the surgical planning software tool is configured to determine a shape and topography of the plate, and wherein the shape and the topography of the plate are designed to mate with the patient's spinal anatomy.

18. The fixation system of claim 16, wherein the surgical planning software tool comprises at least one computer memory that is not a transitory signal, the at least one computer memory comprising instructions executable by at least one processor.

19. The fixation system of claim 16, wherein the one or more measurements include a measurement associated with pelvic tilt, and wherein the one or more predictive guidelines include a pelvic tilt value of less than 20 degrees.

20. The fixation system of claim 16, wherein the one or more measurements include a measurement associated with sagittal alignment, and wherein the one or more predictive guidelines include a sagittal vertebral axis value of less than or equal to 5 cm.

21. The fixation system of claim 16, wherein the one or more measurements include a first measurement associated with lumbar lordosis and second measurement associated with pelvic incidence, and wherein the one or more predictive guidelines include a mathematical rule defined by an absolute value of the difference between pelvic incidence and lumbar lordosis being less than 10 degrees.

* * * * *